United States Patent [19]

Ester

[11] Patent Number: 4,927,816
[45] Date of Patent: May 22, 1990

[54] FORMULAE AND METHODS FOR SUBLINGUAL INGESTION OF NATURAL PROGESTERONE

[76] Inventor: George C. Ester, 9457 118th La., N. Seminole, Fla. 33542

[21] Appl. No.: 87,320
[22] Filed: Aug. 20, 1987
[51] Int. Cl.$^5$ .............................................. A61K 31/56
[52] U.S. Cl. .................................... 514/177; 514/899; 514/951; 514/960
[58] Field of Search ................ 514/951, 960, 899, 177

[56] References Cited

U.S. PATENT DOCUMENTS

| | | |
|---|---|---|
| 3,051,624 | 8/1962 | Lozinski . |
| 3,284,303 | 11/1966 | Meli . |
| 3,535,419 | 10/1970 | Siegrist et al. . |
| 3,755,575 | 8/1973 | Lerner . |
| 4,196,188 | 4/1980 | Besins .................... 514/177 |
| 4,206,209 | 6/1980 | Kracaver ................ 514/163 |
| 4,226,848 | 10/1980 | Nagai et al. ........... 514/960 |
| 4,315,925 | 2/1982 | Hussain et al. ........ 514/177 |
| 4,349,530 | 10/1982 | Royer .................... 424/426 |
| 4,432,975 | 2/1984 | Libby .................... 514/946 |
| 4,439,432 | 3/1984 | Peat ...................... 514/177 |
| 4,539,315 | 9/1985 | Bender et al. .......... 514/960 |

FOREIGN PATENT DOCUMENTS 0258110 12/1985 Japan .................................. 514/177

OTHER PUBLICATIONS

"Bailey's Ind. Oil & Fat Products", Swen D. (Interscience, N.Y.), 1965, pp. 199, 200, 208, 209, 210, 211, 224–226.
"Steroid Solutions", Hoechst, (1958), Chem. Abs. #17632f.

Primary Examiner—H. M. S. Sneed
Assistant Examiner—J. Saba

[57] ABSTRACT

Formulae, means, and methods for the sublingual ingestion of natural Progesterone comprising milling and blending natural Progesterone such that it can be absorbed by the sublingual mucosae of a patient and applying it to said sublingual mucosae in a form which permits such absorption.

12 Claims, 5 Drawing Sheets

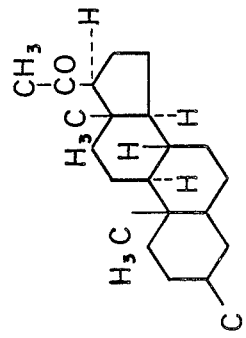
FIG_2
Progesterone [57-83-0] $C_{21}H_{30}O_2$ (314.47)
Progesterone USP
Pregn-4-ene-3,20-dione;
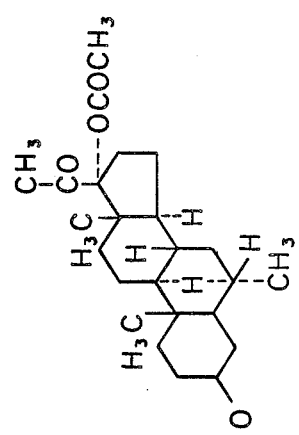
FIG_1
17-Hydroxy-6α-methylpregn-4-ene-3,20-dione acetate [71-58-9] $C_{24}H_{34}O_4$ (386.53)

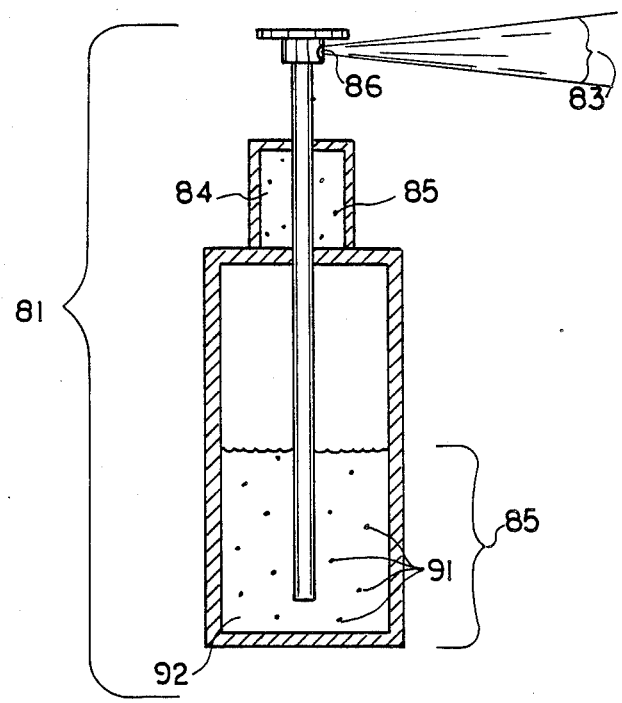
FIG_10
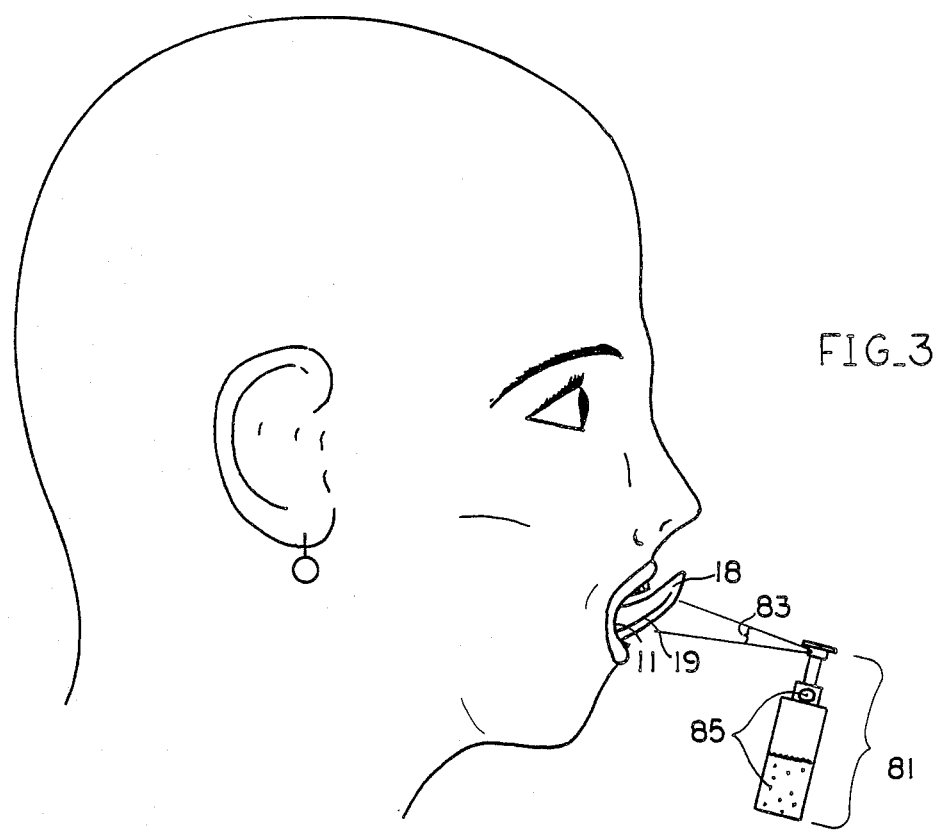
FIG_3

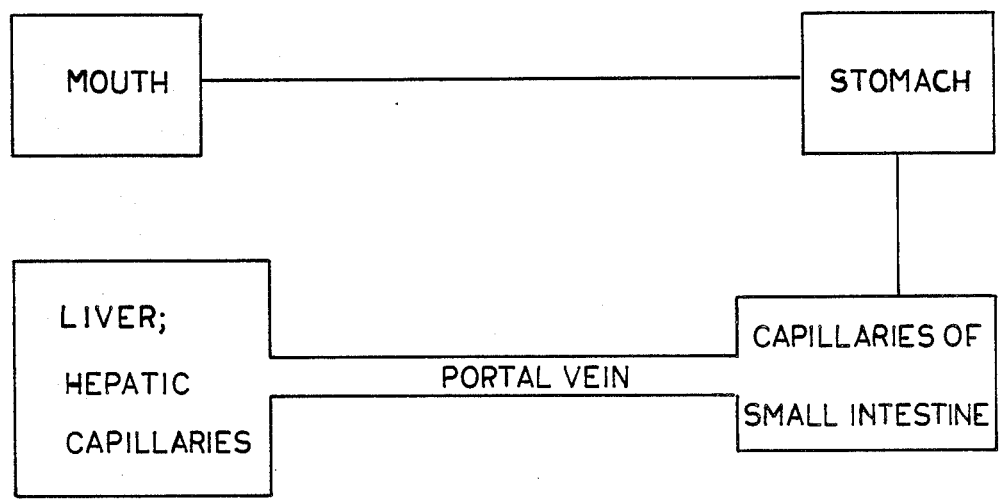
FIG_4
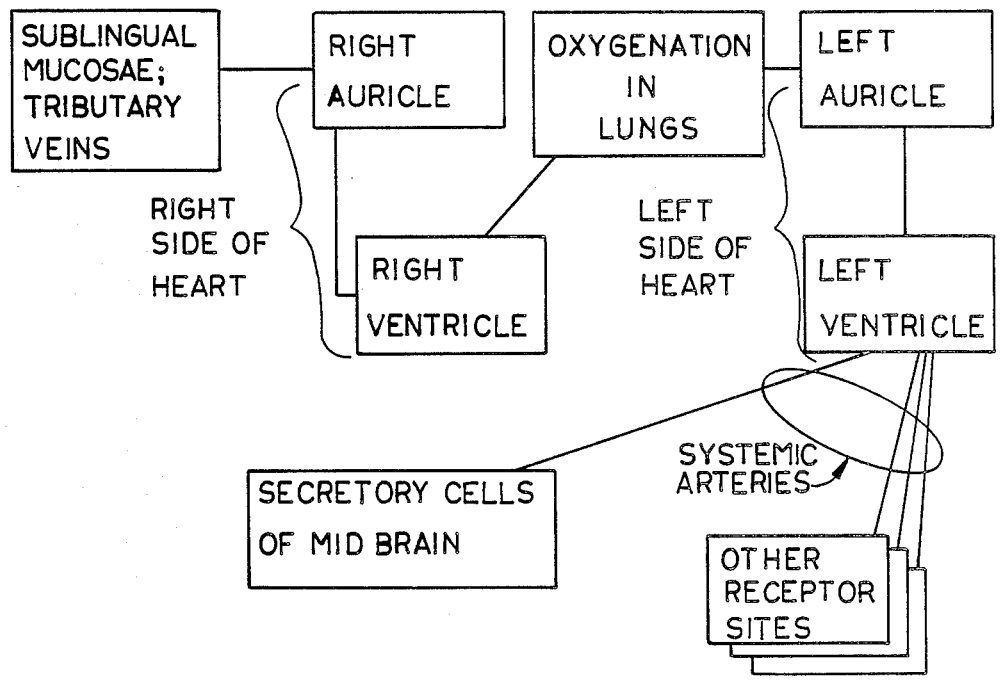
FIG_5

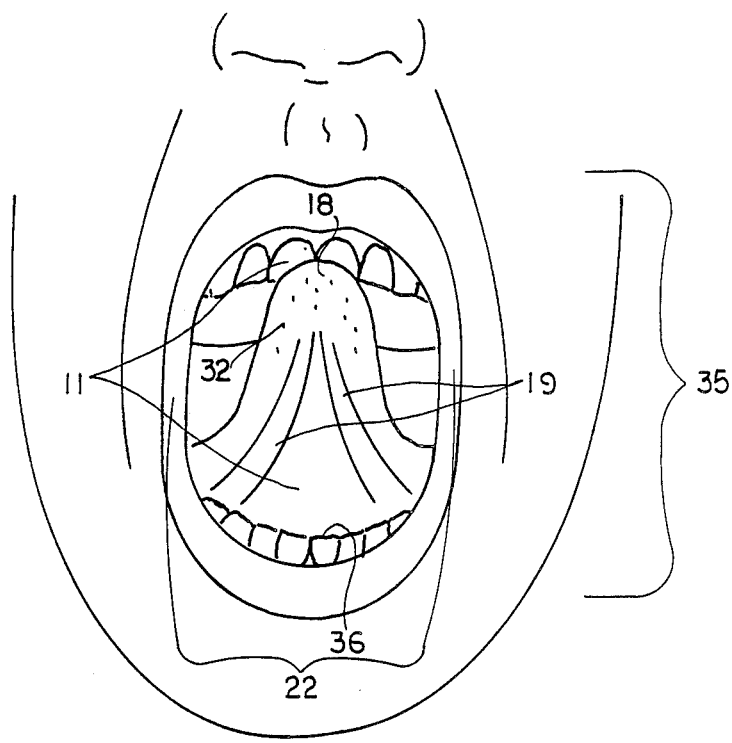
FIG_6
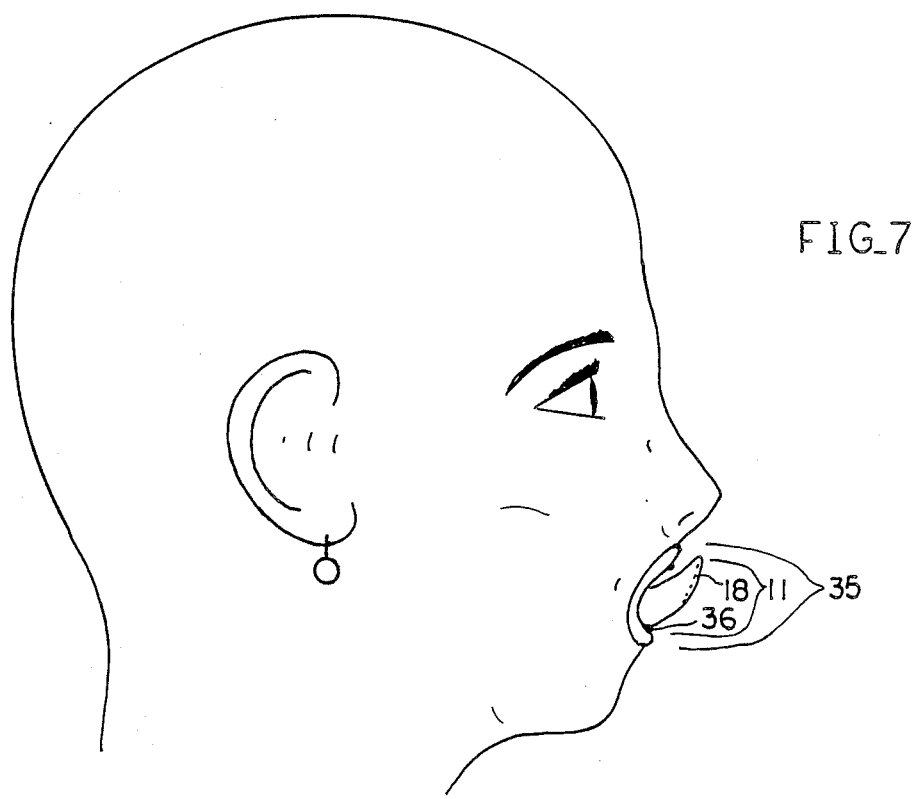
FIG_7

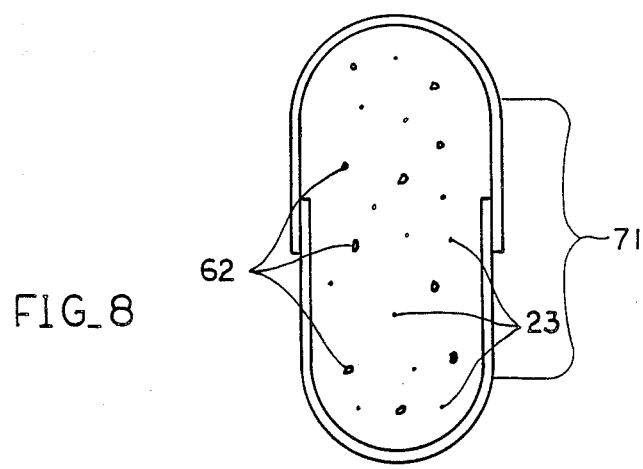
FIG_8
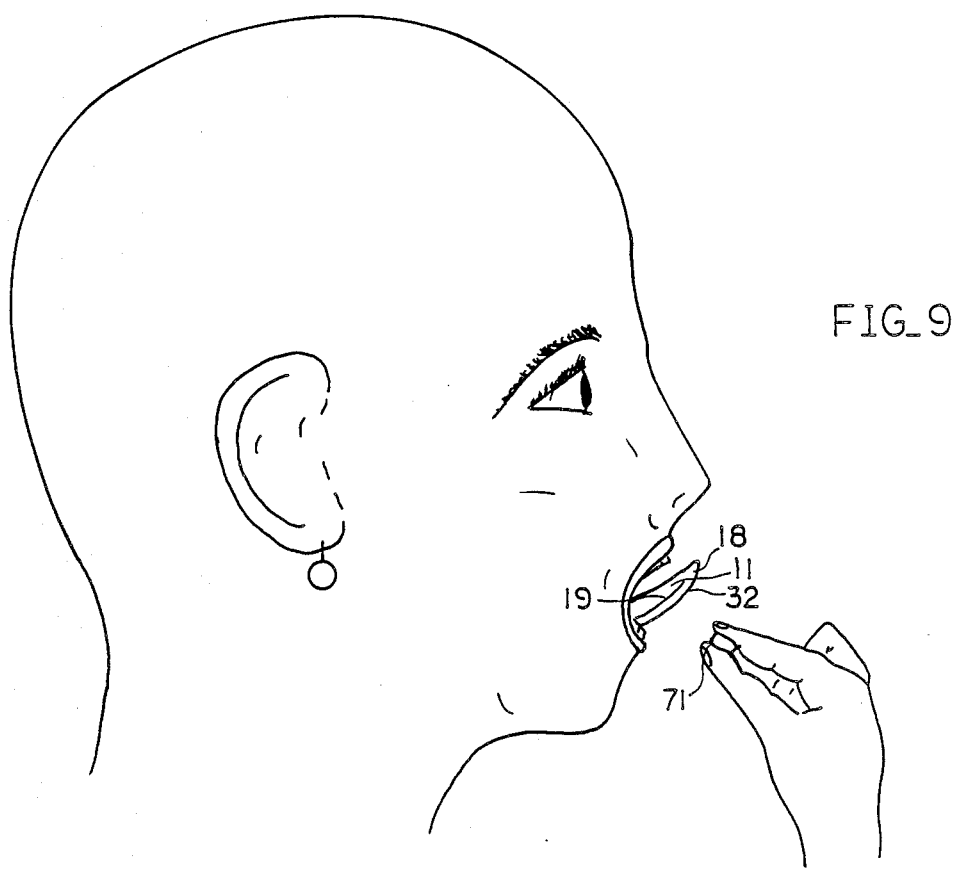
FIG_9

FORMULAE AND METHODS FOR SUBLINGUAL INGESTION OF NATURAL PROGESTERONE

SUMMARY OF THE INVENTION

The invention relates to pharmaceutical methods of preparing and dispensing the hormone Progesterone USP as well as a method of administering same.

Progesterone USP is a natural female body hormone. Under its influence the numerous minute glands which line the uterine cavity are transformed into secreting glands. This alteration is a part of the change which is essential to provide for the implantation of a fertilized ovum and for the continuing development of the placenta.

The present methods of effectively administering natural Progesterone (Progesterone USP) include suppositories, injection, and rectal suspension. Suppositories and injections are clearly the quickest method and, because of their direct access to the bloodstream, they are also the most effective.

The present invention relates to a form of Progesterone USP which is suitable for sublingual ingestion and methods for preparing Progesterone USP for sublingual ingestion. The invention also relates to the method of administering the medicine sublingually. Sublingual administration of the medicine, while resembling oral ingestion in comfort and convenience, has the added advantage of providing a direct path into the bloodstream. This results in a fast and efficient administration of the medicine.

Kincl (U.S. Pat. No. 3,193,457, Apr. 11, 1967) teaches the oral administration of various combinations of synthetic progestogens namely, dimethylprogesterone. It is therein pointed out that oral administration has advantages with respect to patients in a special state of sensitivity and mental stress. Kincl however, requires the dimethylprogesterone to pass through the stomach.

Kincl, however does not teach a method of the administration of Progesterone USP, as depicted in FIG. 1, but requires the use of other synthesized form of the hormone. Another such synthetic progestogen is depicted in FIG. 2.

Progesterone USP is the natural form of the hormone. As such it has the advantage of known compatability with the human body which synthetic forms do not posses. This makes direct application to the bloodstream more feasible than with synthetic forms of the hormone. Additionally, there are certain "receptor sites" within the body which will not accept synthetic forms of Progesterone but will accept and process doses of Progesterone USP. These are the secretory cells of the mid-brain, the lining of the womb, the lungs, the eyes, the breasts, the liver, and the nasopharangeal passages. Any application of Progesterone to these areas must be in the form of Progesterone USP.

A discussion of the processing of the sex hormones, including Progesterone USP within the body is helpful in summarizing the present invention and is schematically depicted in FIG. 3. Progesterone USP is manufactured by the ovaries and transmitted through the bloodstream to the secretory cells of the mid-brain. Here it is processed, along with the other various sex hormones into a variety of anterior pituitary hormones, such as prolactin, somatropic hormone, thyrotropin, adrenocorticotropin, follicle-stimulating hormone, and luteinizing hormone. It is these hormones which, in turn, stimulate healthy body metabolism.

The focus of the present invention is concerned with means and methods of delivering sex hormones, particularly Progesterone USP, to the secretory cells of the mid-brain, or other appropriate receptor sites for further body metabolism.

FIG. 4 depicts the path of medications, including Progesterone USP and other sex hormones, which are orally ingested. Entering the body through the mouth, they are next passed along to the stomach. From there they are processed, without significant chemical breakdown in the case of Progesterone USP, into the small intestines. From the small intestines they are transmitted, through the portal vein, into the liver. Within the liver, most medications, including Progesterone USP, are significantly broken down. For this reason oral ingestion of Progesterone USP is not effective in applications designed to treat deficiencies of the metabolic chain described in FIG. 3.

The sublingual mucosae, located on the underside of a person's tongue, provide expeditious entry into the general bloodstream of the person through the sublingual tributory veins. FIG. 5 schematically depicts the path taken by a medication entering the bloodstream at that point. Such a medication would first need to be absorbed through the sublingual mucosae into the sublingual veins. From there, the medication would be pumped into the right side of the heart and then into the lungs where the blood would be oxygenated. Progesterone USP would not be affected at this point. From there the oxygenated blood would carry the medication back into the left side of the heart and out through the systemic arteries for distribution throughout the body, including the secretory cells of the mid-brain and the other described receptor sites for Progesterone USP.

It would be advantageous to develop a form of Progesterone USP which could be administered without injections or suppositories in order to spare the related pain, inconvenience, or discomfort, yet would still permit quick and efficient entry into the bloodstream. Sublingual ingestion, or ingestion through the mucosae on the underside of a patient's tongue, would resolve this problem.

The present invention describes forms of Progesterone USP suitable for this purpose as well as the methods for milling and blending the Progesterone USP and methods of ingesting the Progesterone USP, so prepared. The invention further describes methods of sublingually administering the medication.

It is, then, an object of the invention to provide a form of pure natural Progesterone (Progesterone USP) which is capable of sublingual ingestion.

It is a further object of the invention to provide various methods of preparing a form of Progesterone USP which is capable of sublingual ingestion.

It is a further object of the invention to provide methods of sublingually administering Progesterone USP.

Further objects and advantages of the invention will become apparent during the detailed description and summary which follow.

BRIEF DESCRIPTION OF THE DRAWINGS

In having set out a background and summary of the invention as well as in the following detailed description of the invention, reference has been and will be made to the figures briefly described herein.

FIG. 1 depicts the chemical structure of a typical synthetic progestogen.

FIG. 2 depicts the chemical structure of Progesterone USP.

FIG. 3 depicts the atomizer application of milled Progesterone USP according to the present invention.

FIG. 4 schematically depicts the path of medicines which are orally ingested.

FIG. 5 schematically depicts the path of medicines which are sublingually ingested.

FIG. 6 is a frontal view of the sublingual cavity.

FIG. 7 is a side view of the sublingual cavity.

FIG. 8 depicts a Progesterone USP capsule according to the present invention.

FIG. 9 depicts the application of a Progesteone USP capsule according to the present invention.

FIG. 10 depicts an atomizer with milled Progeserone USP according to the present invention.

DESCRIPTION OF THE PREFERRED EMBODIMENT

In providing a detailed description of the invention, direct reference will be made to the accompanying figures, numbered 3 and 6 through 10. It may prove helpful, however, to refer back to matters depicted in the previous figures for reference should difficulty be experienced in grasping the nature of the improvements and applications herein described.

Progesterone USP is marketed to the public through pharmacists as a prescription drug. Pharmacists typically receive Progesterone USP in a powder form. The present invention, in its preferred embodiments, is easily adapted from that form by further milling of the Progesterone USP with standard milling equipment. This process is well-known in the art and is not the subject of any claims herein. Consequently, no effort will be made to describe the milling process here, beyond providing data concerning the extend of milling required.

The sublingual area (11) of the mouth (35) is depicted in FIGS. 6 (front view) and 7 (lateral view). It generally comprises the area defined by the underside of the tongue (18) and the floor (36) of the mouth (35). The sublingual mucosae (32) are on the underside (37) of the tongue (18) along with the sublingual tributary veins (38).

Making reference now to FIGS. 8 and 9 the preparation of encapsulated Progesterone for sublingual administration and its sublingual administration will be described. First, Progesterone USP is milled as required such that no less than 75% of the total amount of it is in particle sizes which are less than five microns in diameter (23). The milled Progesterone USP (23) is then mixed with a salivic stimulator (62), such as citric acid. This mixture is then placed in a capsule (71), such as a "Lilly" brand capsule number 2, which is designed to readily dissolve when subjected to salivic juices in amounts normally found in the mouth.

In this form, the capsule can be placed under the patient's tongue (18) into the sublingual area (11). The capsule will quickly dissolve and the citric acid will stimulate the production of salivic fluid within the sublingual mucosae (32), maximizing the rate of sublingual absorption. The Progesterone USP will then be absorbed into the bloodstream (19) through the sublingual mucosae (32).

The concentration of salivic stimulator (62) should be within the range of 0.1 to 5 percent of the total amount of the mixture. There must be enough salivic stimulator to ensure a presence of saliva on the sublingual mucosae (32). Too much saliva could result in significant amounts of the Progesterone USP (23) being carried away for oral ingestion of the Progesterone USP (23). This is precisely the event we seek to avoid because of the resulting premature breakdown of the medicine.

While citric acid is perhaps one of the more efficient salivic stimulators for use in this manner, a number of others, in the same relative concentrations, could be substituted. Some of the others which would be approved for use in this manner would be citric acid syrup, cherry juice, cherry juice syrup, cinnamon, cinnamon oil, clove oil, dextrose, ginger, glucose, lemon oil, lemon tincture, methyl salicylate, various orange extracts, various peppermint extracts, raspberry juice, raspberry syrup, various forms of saccharin, sorbitol, spearmint, spearmint oil, sucrose, syrup, various vanilla extracts, wild cherry syrup, and aspertame.

Alternate embodiments of the invention are depicted in FIGS. 3 and 10 In these embodiments of the invention, the Progesterone USP is prepared in such a manner as to permit application through an atomizer and the Progesterone USP is sublingually administered through an atomizer. Making reference first to FIG. 10, Progesterone USP is milled as required to facilitate its emulsification within fluids fit for human consumption. The fluids are used exclusively as an atomizer propellant vehicle. They must also be such that no chemical modification of the Progesterone USP will take place.

The milled Progesterone USP (91) emulsified within a suitable fluid (92) is then placed in an atomizer, generally (81), which is further adapted with an actuator (84). The actuator (84) is calibrated so as to accept only a precisely measured volume of the emulsified Progesterone USP (85) available for each application.

The operation of atomizers in providing a spray of fluids through a nozzle is well known in the art and not the subject of any claims herein. Consequently the functional principles of atomizers will be neither described nor depicted here, except to point out that the milling of the Progesterone USP must be sufficient to ensure that the particles of milled Progesterone emulsified within the fluid must be small enough to pass through the nozzle (86) of the atomizer (81). The nozzle (86) must be adapted to produce a spray the limits of which can easily be confined within the limits of a person's tongue (18).

Any concentration of Progesterone USP which permits its full emulsification within the fluid is acceptable. Natural oils, such as sesame seed, peanut, or vegetable oil are suitable for use as the propellant fluid.

One acceptable atomizer is manufactured by "Valois" of West Germany. It is equipped with a model number DF10 valve, which is 20 mm in length, an actuator model number 251 and an insert model number GP3. It should be noted that this method could be practiced with either a manually pumped or pressurized atomizer apparatus, so long as the pressure is sufficient to drive the emulsified Progesterone USP (85) through the atomizer and the atomizer was further equipped with an accurate actuator.

Making reference to FIG. 3, the administration of emulsified Progesterone USP (85) according to the present invention is described. The patient's tongue (18) is lifted and the blend (85) is sprayed against the underside (37) of the tongue, or into the sublingual area (11), again permitting immediate absorption into the bloodstream (19) through the sublingual mucosae (32). FIG.

11 depicts the use of an atomizer (81) which is capable of precisely directing a band of spray (82) with radius (83) which is less than the width (22) of the patient's tongue (18).

Certain other modifications and embodiments of the invention as have been described herein may be made without departing from the spirit or the scope thereof and it is to be understood that the invention is to be limited only as defined in the appended claims.

What is claimed is:

1. A pharmaceutical formula for the administration of Progesterone USP said formula comprising;
    Progesterone USP milled such that at least seventy-five percent of the total amount is composed of particle sizes of less than five microns diameter;
    said Progesterone USP being blended with a salivic stimulator in an amount adapted to stimulate sufficient saliva to dissolve said milled Progesterone USP but not enough to result in significant oral ingestion of Progesterone USP;
    said mixture of Progesterone USP and salivic stimulator encapsulated within a soluble capsule.

2. The pharmaceutical formula described in claim 1 wherein said salivic stimulator is any combination of one or more of the flavoring materials selected from the list comprising;
    citric acid, citric acid syrup, cherry juice, cherry juice syrup, cinnamon, cinnamon oil, clove oil, dextrose, ginger, glucose, lemon oil, lemon tincture, methyl salicylate, orange extract, peppermint extract, raspberry juice, raspberry syrup, saccharin, sorbitol, spearmint, spearmint oil, sucrose, syrup, vanilla extract, wild cherry syrup, and aspertame.

3. A method of preparing Progesterone USP such that it can be sublingually administered, said method comprising the steps of;
    milling Progesterone USP such that at least seventy-five percent of said Progesterone USP is in particle size of no more than five microns diameter;
    mixing said Progesterone USP with a salivic stimulation material; and
    encapsulating said mixture within a capsule which is adapted to rapidly dissolve in the presence of saliva.

4. The pharmaceutical formula described in claim 1 wherein the salivic stimulator is citric acid in a concentration of between one-tenth percent and five percent of the entire formula.

5. The pharmaceutical formula described in claim 2 wherein the concentration of said salivic stimulators is between one-tenth percent and five percent of the entire formula.

6. A method for sublingually administering Progesterone USP comprising the steps of,
    suspending Progesterone USP within a fluid which is fit for human consumption and suitable for use as an atomizer propellant;
    spraying said suspended Progesterone USP directly upon the underside of the tongue of the patient and permitting said suspended Progesterone USP to be sublingually absorbed into said patient's bloodstream.

7. A sublingually ingestable form of Progesterone USP, said form comprising,
    Progesterone USP suspended within a suitable propellant fluid;
    said suitable propellant fluid being fit for human consumption and of such density that said suspended Progesterone USP can be passed through an atomizer nozzle.

8. A method of administering Progesterone USP, comprising the steps of;
    milling Progesterone USP such that at least seventy-five percent of said Progesterone USP is in particle size of no more than five microns diameter;
    mixing said Progesterone USP with a salivic stimulation material;
    encapsulating said mixture within a capsule which is adapted to rapidly dissolve in the presence of saliva; and
    placing said encapsulated Progesterone USP between the lower surface of the patient's mouth and the underside of the patient's tongue.

9. A method of sublingually administering Progesterone USP comprising the steps of;
    milling the Progesterone USP to a size small enough to pass through the nozzle of an atomizer;
    suspending said milled Progesterone USP within a suitable fluid which is suitable for human consumption and will neither break down nor change the chemical nature of said suspended Progesterone USP; and
    placing said suspended Progesterone USP into an atomizer; and
    spraying said suspended Progesterone USP upon the underside of the patient's tongue.

10. The method described in claim 9, in which said suitable fluid is peanut oil.

11. The method described in claim 9, in which said suitable fluid is sesame seed oil.

12. The method described in claim 9, in which said suitable fluid is vegetable oil.

* * * * *